(12) United States Patent
Hsueh et al.

(10) Patent No.: US 12,036,371 B2
(45) Date of Patent: *Jul. 16, 2024

(54) METHOD OF ACCESSING THE LEFT ATRIUM WITH A MULTI-DIRECTIONAL STEERABLE CATHETER

(71) Applicant: BioCardia, Inc., Sunnyvale, CA (US)

(72) Inventors: Wai Hsueh, Sunnyvale, CA (US); Ken Vien, Sunnyvale, CA (US); James B. Ross, Sunnyvale, CA (US)

(73) Assignee: BioCardia, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,237

(22) Filed: Apr. 3, 2023

(65) Prior Publication Data

US 2023/0233805 A1 Jul. 27, 2023

Related U.S. Application Data

(63) Continuation of application No. 17/472,629, filed on Sep. 11, 2021, now Pat. No. 11,617,859, which is a continuation of application No. 16/113,556, filed on Aug. 27, 2018, now Pat. No. 11,141,568, which is a continuation of application No. 14/887,203, filed on Oct. 19, 2015, now abandoned.

(51) Int. Cl.
*A61M 25/01* (2006.01)
*A61F 2/24* (2006.01)
*A61B 18/14* (2006.01)

(52) U.S. Cl.
CPC .... *A61M 25/0136* (2013.01); *A61M 25/0147* (2013.01); *A61B 18/1492* (2013.01); *A61F 2/2427* (2013.01)

(58) Field of Classification Search
CPC .......... A61M 25/0136; A61M 25/0053; A61M 25/0147; A61M 25/0012; A61M 25/005; A61M 25/0105; A61M 25/0026; A61M 25/0045; A61M 25/0116; A61M 25/0133
See application file for complete search history.

(56) References Cited

U.S. PATENT DOCUMENTS

| | | | |
|---|---|---|---|
| 5,358,478 A | 10/1994 | Thompson | |
| 6,080,117 A | 6/2000 | Cornelius | |
| 7,374,553 B2 | 5/2008 | Koerner et al. | |
| 9,101,733 B2 | 8/2015 | McDaniel | |
| 11,141,568 B2 * | 10/2021 | Hsueh | A61M 25/0136 |
| 11,617,859 B2 | 4/2023 | Hsue | |

(Continued)

OTHER PUBLICATIONS

Shah, S., Gnanasegaran, G., Sundberg-Cohon, J., Buscombe, J. (2009). The Heart: Anatomy, Physiology and Exercise Physiology. In: Movahed, A., Gnanasegaran, G., Buscombe, J., Hall, M. (eds) Integrating Cardiology for Nuclear Medicine Physicians. Springer, Berlin, Heidelberg. (Year: 2009).*

(Continued)

*Primary Examiner* — Tasnim Mehjabin Ahmed
(74) *Attorney, Agent, or Firm* — Crockett & Crockett, PC; K. David Crockett, Esq.

(57) ABSTRACT

A bi-directional steerable catheter adapted for delivery into a patient's vasculature. The pull wires which are used to tension the deflectable segment of the steerable catheter are wound in parallel around the axis of the steerable catheter on opposite sides of the steerable catheter.

7 Claims, 4 Drawing Sheets

(56) References Cited

U.S. PATENT DOCUMENTS

| | | |
|---|---|---|
| 2004/0015151 A1 | 1/2004 | Chambers |
| 2004/0059288 A1 | 3/2004 | Webler |
| 2006/0135961 A1 | 6/2006 | Rosenman et al. |
| 2006/0252993 A1 | 11/2006 | Freed |
| 2007/0088244 A1 | 4/2007 | Miller |
| 2009/0318835 A1 | 12/2009 | Ressemann et al. |
| 2011/0282379 A1 | 11/2011 | Lee |
| 2012/0123327 A1* | 5/2012 | Miller ............... A61M 25/0136 604/95.04 |
| 2012/0209073 A1 | 8/2012 | McWeeney |
| 2015/0174363 A1 | 6/2015 | Sutermeister |
| 2015/0258306 A1 | 9/2015 | Plassman |
| 2018/0279994 A1* | 10/2018 | Schaer ................. A61B 8/4466 |

OTHER PUBLICATIONS

International Search Report and Written Opinion dated Feb. 3, 2017 from PCT Application No. PCT/US2016/057675.

* cited by examiner

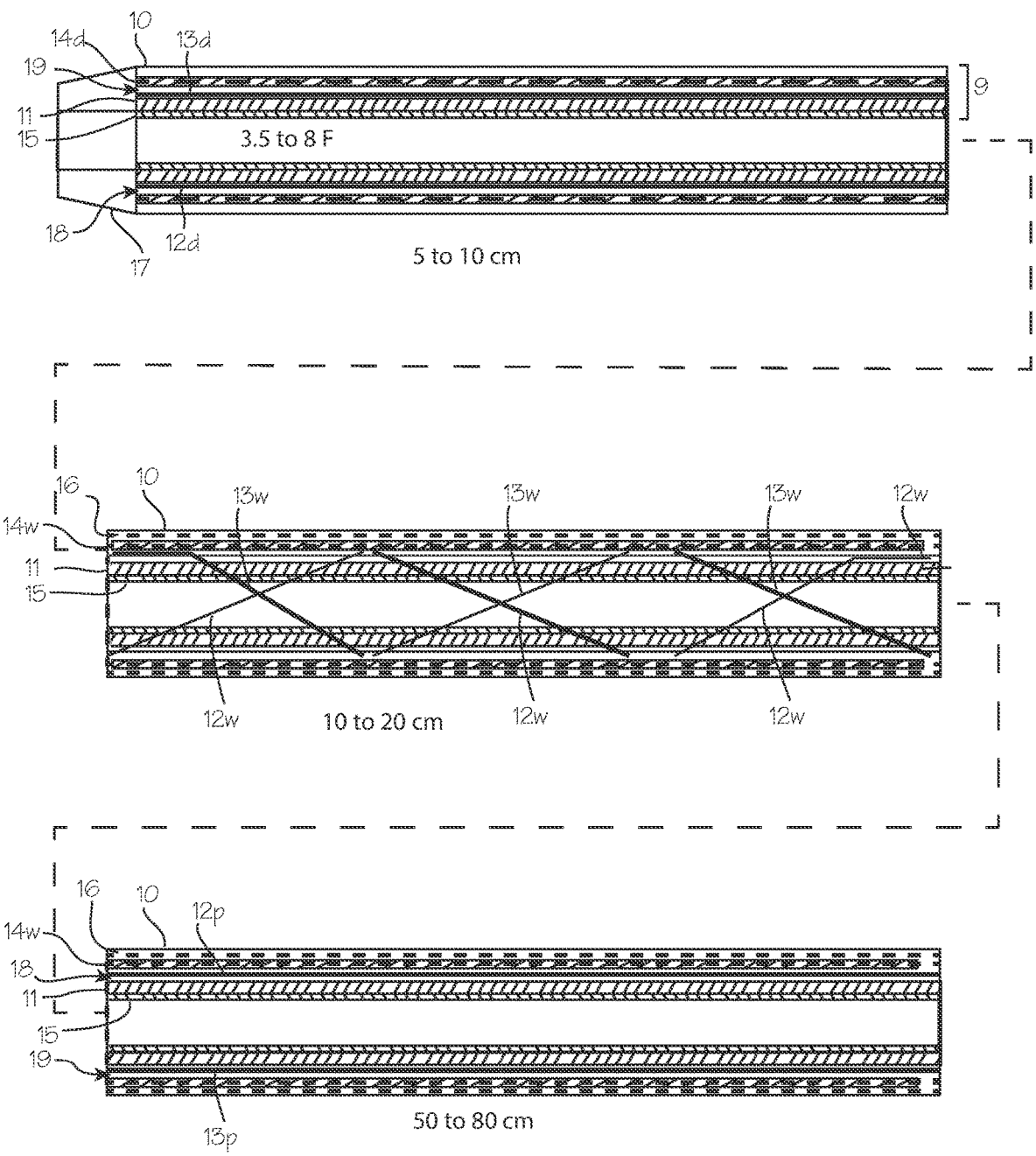

METHOD OF ACCESSING THE LEFT ATRIUM WITH A MULTI-DIRECTIONAL STEERABLE CATHETER

This application is a continuation of U.S. application Ser. No. 17/472,629 filed Sep. 11, 2021, now U.S. Pat. No. 11,617,859, which is a continuation of U.S. application Ser. No. 16/113,556 filed Aug. 27, 2018, now U.S. Pat. No. 11,141,568, which is a continuation of U.S. application Ser. No. 14/887,203 filed Oct. 19, 2015, abandoned.

FIELD OF THE INVENTION

The inventions described below relate to the field of steerable guide catheters, sheaths and introducers.

BACKGROUND OF THE INVENTIONS

Steerable catheters, including steerable guide catheters, guide sheaths and introducer sheaths, are used to gain access to the desired target location within the vasculature of a patient and provide a safe, smooth conduit to guide and support another device, such as an interventional catheter, to a target location in the vasculature of a patient. The interventional catheter is typically a delivery device that carries an implant for deposit in the vasculature, or an active device that carries out the diagnosis, therapy or intervention. Guide catheters, guide sheaths and introducer sheaths can also be used to pass fluids for visualization, diagnosis or treatment. Provision of steering mechanisms in these catheters facilitates their navigation through the vasculature of a patient, to gain access a target site.

SUMMARY

The steerable catheters described below provide for easy, atraumatic access to areas of the vasculature that are otherwise difficult to access, while minimizing the propensity of pull-wire operated steerable catheters to whip, or rapidly snap from one configuration to another, as the pull wire is tensioned to steer the device. The steerable catheters described below are constructed with components that are selected to provide optimal stability to prevent whipping. The steerable catheter includes two or more pull wires which are wound along a portion of the steerable catheter, around the long axis of the steerable catheter, in parallel and circumferentially on opposite sides of the steerable catheter, to balance the off-axis forces applied by the pull wires, and thus prevent whipping and avoiding changes in curve geometry achieved by manipulation of the pull wires when the steerable catheter is deployed within the vasculature such that the wound portion of the steerable catheter runs through a bend in the vasculature. The curve in the vasculature may be any tortuosity such as the aortic arch, the iliac bifurcation, the atrial septum, the brachial artery inlet from the aorta, etc. The deflection segment curve geometry remains more stable when the steerable catheter is rotated around its long axis. The minimization of whipping is very effective, and the deflection segment curve geometry remains more stable, where the steerable catheter components are arranged along the length of the steerable catheter such that the wound segments coincide with the expected bend in the vasculature in the vasculature in which it is deployed.

BRIEF DESCRIPTION OF THE DRAWINGS

FIG. 4 is a cross section of the steerable catheter of FIG. 1.

DETAILED DESCRIPTION OF THE INVENTIONS

Figure 1:
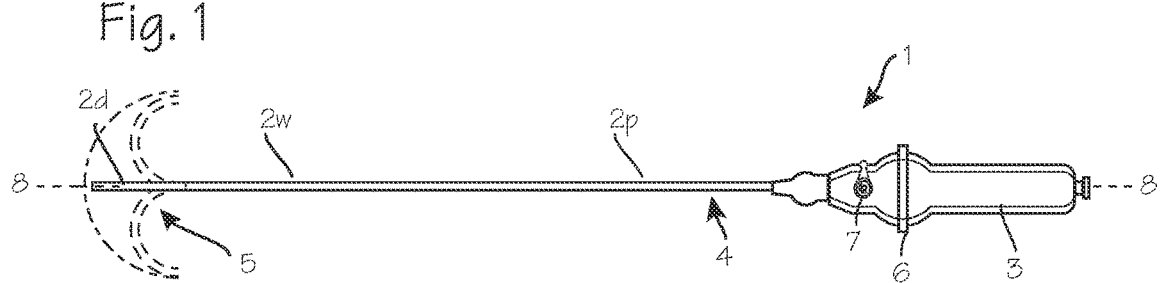
FIG. 1 illustrates the steerable catheter.

FIG. 1 illustrates the deflectable steerable catheter. The steerable catheter 1 comprises a steerable catheter tube 2 with a catheter handle 3 mounted on the proximal end 4 of the steerable catheter tube and a deflectable segment at the distal end 5, and a lumen extending through the tube. The steerable catheter tube includes the first, deflectable segment 2d which is operated by a pull wire, a second, wound segment 2w (extending proximally from the first segment) in which the pull wires are wound around the catheter (shown in FIGS. 2 through 4), and, optionally, a third, proximal segment 2p (extending proximally from the second segment), in which the pull wire runs straight on opposite sides of the steerable catheter tube. The catheter handle includes a steering lever 6, which can be turned by a user to manipulate an internal steering mechanism (show in FIGS. 5 and 6) and the pull wires, and thus deflect the deflectable segment in to an arcuate configuration, and a brake 7 which can be manipulated to lock the steering mechanism in any selected position and thus hold the deflectable segment in an arcuate configuration selected by the user of the device, and corresponding to the rotational position of the steering lever. As shown in phantom, the deflectable segment 2d is operable, through manipulation of the steering lever, to bend through a significant arc, away from the longitudinal axis 8, in two directions in the same plane (where two pull wires are provided), so that the tip can be deflected through an arc intersected by the longitudinal axis, without the need to rotate the steerable catheter about the longitudinal axis. This behavior is referred to bi-directional steering.

Figure 2:
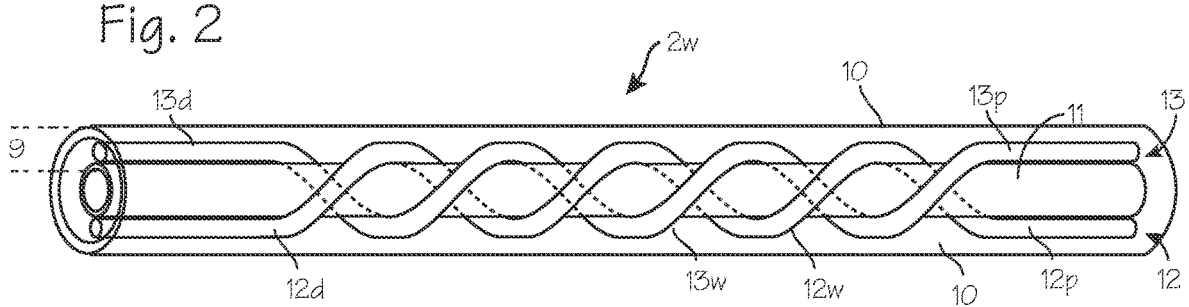
FIGS. 2 and 2A are schematic views of the steerable catheter with wound pull wires.
Figure 3:
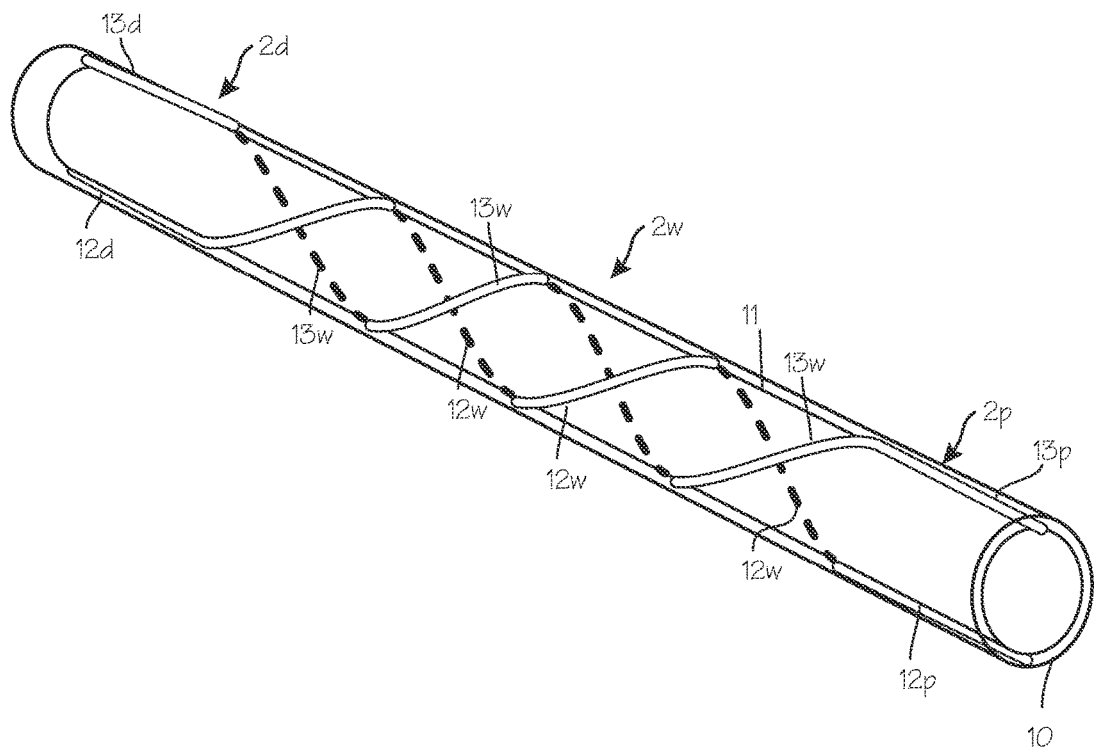
FIG. 3 is a perspective view of the steerable catheter and the wound pull wires.

FIGS. 2 and 3 illustrate the steerable catheter and wound pull wires embedded within the catheter wall and arranged to provide steering without whipping. The major components of steerable catheter tube 2 include the catheter wall 9 comprising an outer tube or jacket 10 and an inner tube 11, and two pull wires 12 and 13 disposed between the outer tube and the inner tube. In the wound segment of the steerable catheter (2w in FIG. 1), the pull wires are wound about the longitudinal axis of the tube, and each pull wire is wound in the same direction as the other pull wire in wound wire segments 12w and 13w, preferably substantially in parallel, to create a segment of the steerable catheter in which the pull wires are wound on circumferentially opposite sides of the steerable catheter at each point along the length of the wound segment 2w (that is, in any radial cross section, the wound wires will be on opposite sides of the steerable catheter, though along the s of the wound segment the pull wire wrap around the steerable catheter). Each pull wire has a straight distally extending segment 12d and 13d, extending from the wound segment, toward the distal end of the steerable catheter (corresponding to the deflectable segment 2d in FIG. 1), and a straight proximally extending segment 12p and 13p extending proximally from the wound segment toward the proximal end of the steerable catheter (corresponding to the proximal segment 2p in FIG. 1), where they are fixed to the control mechanism shown in FIG. 4. The straight distally extending segments 12d and 13d correspond to the deflectable segment 2d of FIG. 1. The pull wires may be disposed within separate side lumens 18 and 19 in the wall of the inner tube or outer tube or they may be disposed within separate smaller tubes secured over the inner tube.

Figure 2A:
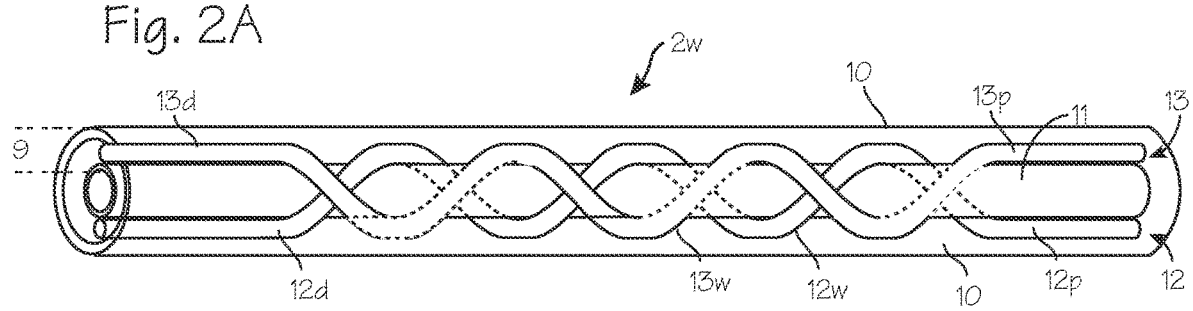

As shown in FIG. 2A, in the wound segment of the steerable catheter (item 2w in FIG. 1), the pull wires may be counter-wound, rather than parallel, with each pull wire wound in a direction opposite the other pull wire in wound wire segments 12w and 13w, to create a segment of the steerable catheter in which the pull wires are counter-wound. The counter-wound segments of the pull wires may be wound with one pull wire within the other, or they may be braided.

FIG. 4 is cross section of the steerable catheter, showing additional layers of the steerable catheter. As shown in FIG. 4, the deflectable segment 2d of the steerable catheter tube 2 consists of the inner tube 11, and straight distally extending segments 12d and 13d of the pull wires (disposed on opposite side of the steerable catheter, about 180° apart, both within 0.001" thick PTFE pull wire liners), the deflectable segment also includes a braid 14d (1 over 1 under, 20-30 picks per inch), over the inner tube 11 and the pull wires, all within the outer tube 10. Where the inner tube comprises PTFE, no liner may be necessary, but in alternative embodiments in which the inner tube comprises another polymer, the deflectable segment may consist of, in addition to the layers just listed, a PTFE liner 15, disposed within the inner tube. The braid 14d may be embedded in a low durometer polymer, in which case the deflectable segment may consist of, in addition to the layers listed above, the braid embedded in a low durometer polymer.

A segment 2w proximal to the deflectable segment, in which the two pull wires are wound about the axis of the steerable catheter, consists of the inner tube 11, then the wound segments of the pull wires (12w and 13w), a second braid segment 14w (1 over 2 under, at 70-80 picks per inch), within the outer tube 10. (The second braid segment 14w may be an continuous extension of the braid 14d in the deflectable segment, or it may be a discrete additional component.) Again, where the inner tube comprises PTFE, no liner may be necessary, but in alternative embodiments in which the inner tube comprises another polymer, the wound segment 2w may consist of, in addition to the layers just listed, the PTFE liner 15, disposed within the inner tube. The braid 14w may be embedded in a high durometer polymer, in which case the deflectable segment may consist of, in addition to the layers listed above, the braid embedded in a high durometer polymer. An additional braid 16 may be embedded in the outer tube (this braid extends proximally to the pull wire exit at the proximal end of the tube, and is preferably wound at 80 picks per inch for some applications, and 20 picks per inch for other applications). Where, in alternative embodiments, the additional braid 16 is used, the wound segment 2w may consist of, in addition to the layers listed above (the inner tube 11, the pull wires 12 and 13, the braid 14w and the outer tube 10, or the liner 15, the inner tube 11, the pull wires 12 and 13, the braid 14w and the outer tube 10), the additional braid 16.

A third, proximal-most segment 2p, in which the two pull wires run straight along the length of the catheter, from the wound segments of the pull wire to connections in the handle, consists of, or comprises, the inner tube 11, the second braid 14w (the same braid as in the wound segment) (1 over 2 under, at 70-80 picks per inch), then the straight segments of the pull wires (12p and 13p) within the outer tube 10. Again, where the inner tube comprises PTFE, no liner may be necessary, but in alternative embodiments in which the inner tube comprises another polymer, the proximal segment may consist of, in addition to the layers just listed, the PTFE liner 15, disposed within the inner tube. The braid 14w may be embedded in a high durometer polymer, in which case the deflectable segment may consist of, in addition to the layers listed above, the braid embedded in a high durometer polymer. As in the wound segment, the additional braid 16 may be embedded in the outer tube in the third, proximal-most segment 2p. Where, in alternative embodiments, the additional braid 16 is used, the wound segment 2w may consist of, in addition to the layers listed above (the inner tube 11, the pull wires 12 and 13, the braid 14w and the outer tube 10, or the liner 15, the inner tube 11, the pull wires 12 and 13, the braid 14w and the outer tube 10), the additional braid 16.

A soft tip 17 covers the distal tip of the device. The hardness of the outer tube can be very soft at the distal tip at 35D, and transition to progressively harder formulation of 55D proximate the distal end of the wound segment, and then transition further to a harder formulation of about 72D proximate the proximal end of the wound segment, and remain at about 72D or harder for the remaining proximal portion of the steerable catheter.

While the steerable catheter is illustrated with two pull wires, the benefits of the wound pull wires can be achieved with a plurality of pull wires obtain steerability across several planes. For example, the steerable catheter may comprise three or four pull wires, dispersed (preferably evenly distributed) about the circumference of the steerable catheter and wound substantially in parallel in the wound segment, to provide steering along arcs lying in additional planes.

Figure 5:
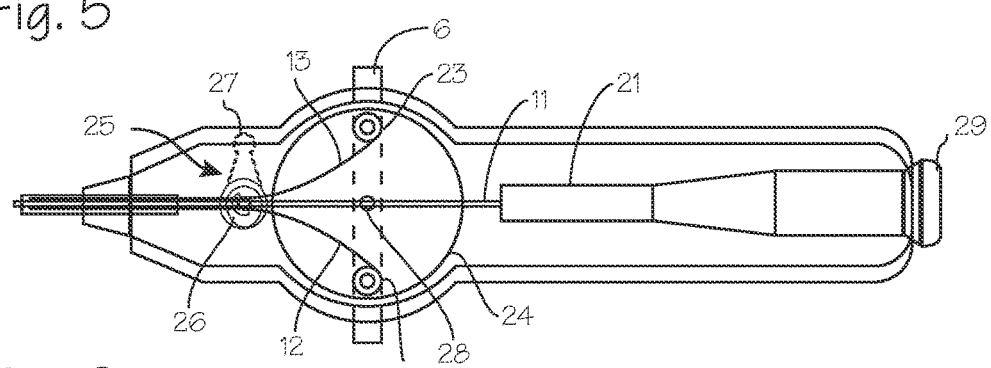
FIGS. 5 and 6 illustrate the control handle of the deflectable steerable catheter of FIG. 1.
Figure 6:
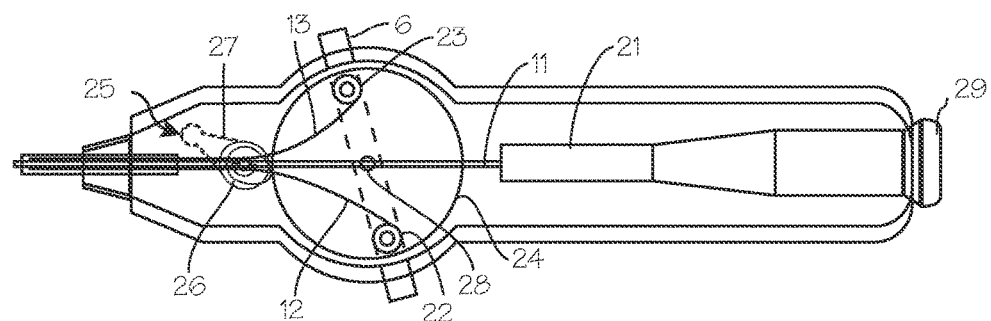

FIGS. 5 and 6 illustrates the catheter handle of the deflectable steerable catheter of FIG. 1, with a braking system that can be used with the pull wire system of FIGS. 1 through 4. The catheter handle 3 is fixed to the steerable catheter tube 2. The inner tube 11 of the catheter extends through the catheter handle to the feeder tube 21, so that working catheters can be fed into the steerable catheter. The proximal tips of the pull wires 12p and 13p are fixed to the steering lever 6 at joints 22 and 23, through any convenient means. In order to provide a mechanism to hold the lever and pull wires in a chosen position, to maintain an arcuate configuration of the deflectable segment, the lever is also rotationally fixed to the round disc 24, which turns in tandem with the pull wire joints 22 and 23, and a brake 7 comprising a cam plate 26 and lever 27 is disposed on the handle such that the rotation of the brake lever rotates cam plate into interfering contact with the disc and prevents the disc from rotating. The brake lever and cam plate are held in position by friction between the lever and cam and the fittings use to connect them to the housing. This is shown in FIG. 6, in which the steering lever has been rotated about its fulcrum 28 (with each pull wire fixed to the lever on opposite sides of the fulcrum) to pull the pull wire 12 proximally, while relieving tension and allowing pull wire 13 to translate distally, and the braking lever has been rotated to jam the cam plate into interfering contact with the disc to hold it in place. Though this braking system is particularly suited for use with the pull wire system of FIGS. 1 through 5, the advantages of the braking system can be obtained with other pull wire systems, and the advantages of the pull wire system can be used with other braking systems. A hemostatic valve 29 is provided at the proximal end of the feeder tube 21.

The inner and outer tube may comprise PEBAX® 7033 SA01 MED WITH FOSTER Propell, or ProPell™ thermoplastic polyurethane (TPU) for the inner tube. The liner, when used, may comprise PTFE. The braids may comprise stainless steel braids of between 25 and 100 picks per inch, or the more preferable pick counts expressed above. The braids are preferably made of flat wire about 0.007" wide by 0.001" thick in a 5.5 French internal diameter configuration and may be larger in larger configurations and smaller in smaller configurations. The braid of the deflectable segment is preferably embedded in a low durometer polymer such as Pebax at 30D to 35D. The braid of the wound segment is preferably embedded in a high durometer polymer such as Pebax at about 72D. The braid of the deflectable segment can be annealed to increase its flexibility, by, for example, heating the stainless steel braid at high temperature (about 1100° F., or 600° C.) for about two minutes. The pull wires are preferably stainless steel round pull wires with a diameter of about 0.006" or flat pull wires about 0.010" wide by 0.003" thick covered in a PTFE liner with a wall thickness of about 0.001". The pull wires may also comprise a stainless steel braid, or a para-aramid synthetic fiber) (Kevlar® tension element. The resultant overall wall thickness for a steerable catheter with a 5.5 F internal diameter, in the deflectable segment and wound segment, may be about 0.3 to 0.4 mm, preferably about 0.367 mm (about 1.1 F). The resultant overall wall thickness for a steerable catheter with an 11 F internal diameter, in the deflectable segment and wound segment, may be about 0.6 to 0.8 mm, preferably about 0.734 mm (about 2.2 F). In such larger diameter cross sections and walls, larger cross sectional area for pull wires and for braid wire material may be used. (Likewise in smaller diameter devices than the 5.5 French internal diameter configuration disclosed these cross sectional areas could be smaller.) These parameters may be varied to adjust the torque transmission, pushability and trackability of steerable catheters for particular applications. Suggested overall dimensions of the steerable catheters for particular applications are as follows:

| Clinical Applications/ Target Site | Proximal Segment | Wound segment | Defl. Segment | ID |
|---|---|---|---|---|
| Femoral vein access across the atrial septum access of the left atrium for AF ablation | 55 cm | 10 cm | 5 cm | 8.5F |
| Femoral vein access across the atrial septum to the left atrium for mitral valve repair | 55 cm | 10 cm | 5 cm | 8.5F, 10.5F 12.5F 14.5 F |
| Femoral artery access across the aortic arch for left ventricular procedures from femoral access for transendocardial biotherapeutic intervention and coronary artery intervention and peri-valvular leak, | 80 cm | 15 cm | 5 cm | 3.5F 4.5F 5.5 F |
| Femoral artery access across the aortic arch for left ventricular procedures from femoral access for aortic valve implantation | 80 cm | 15 cm | 5 cm | 12F 14F 16F 18F 20F |
| Radial artery access to the peripheral vasculature of the aorto ostial region for peripheral interventions | 50 cm | 15 cm | 40 cm | 4.5 F 5.5 F |
| Radial artery access to the peripheral vasculature superior femoral artery for peripheral interventions | 50 cm | 20 cm | 70 cm | 4.5 F 5.5 F |
| Radial artery access to the Aortic arch cardiac interventions such as peri-valvular leak, transendocardial delivery | 50 cm | 20 cm | 10 cm | 3.5F 4.5F 5.5F |
| Carotid access | 80 cm | 15 cm | 5 cm | 3.5F 4.5F 5.5F |

Figure 7:
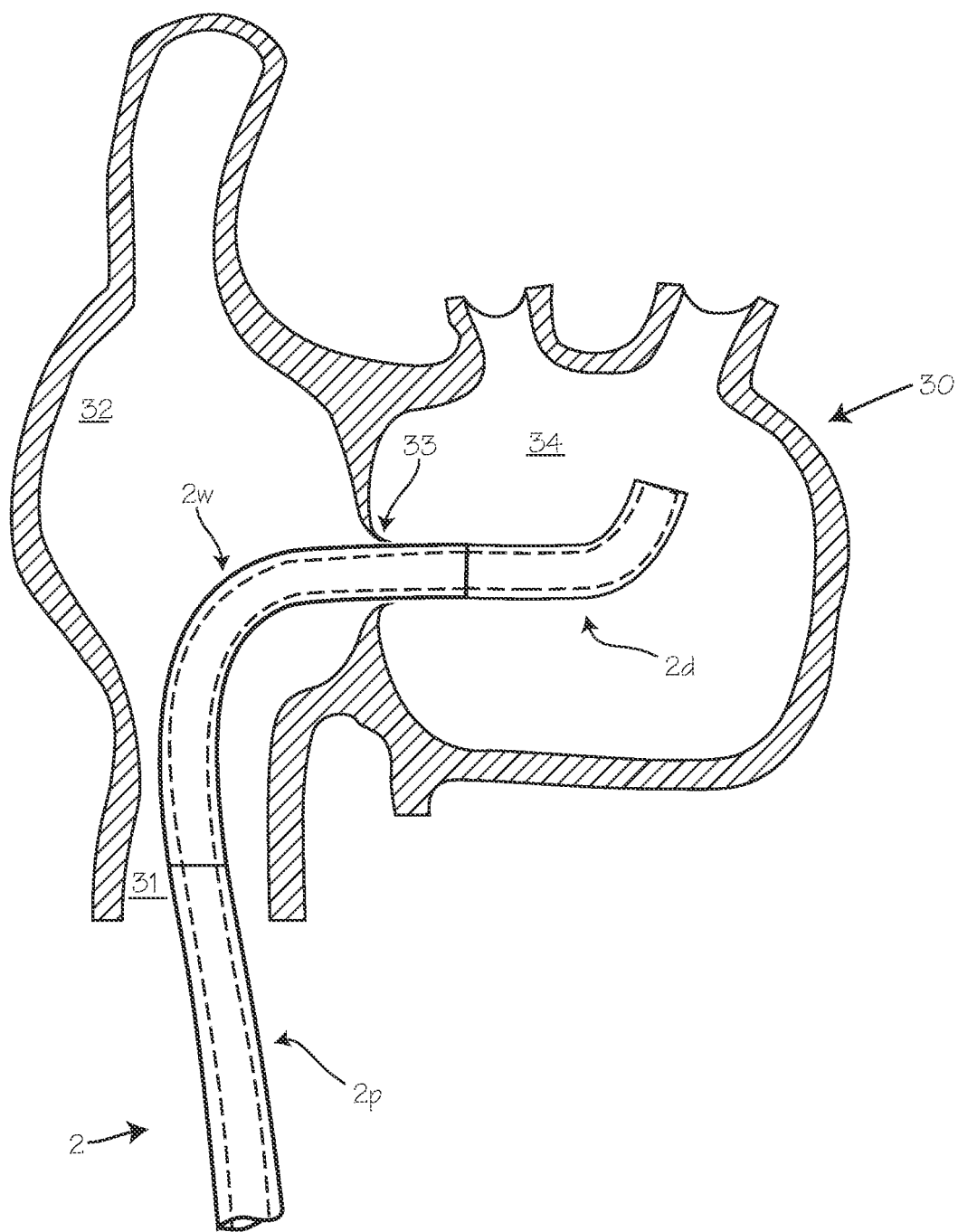
FIG. 7 illustrates the steerable catheter disposed within the vasculature of a patient

Given these dimensions and the typical size and anatomy of patients, the steerable catheter components are arranged along the length of the steerable catheter such that the wound segments coincide with the expected bend in the vasculature on along predetermined access routes. Generally, the steerable catheter is constructions with dimensions for the deflectable segment and the wound segment such that, when inserted through a predetermined access point, with the deflectable segment disposed at a target site, the wound segment is disposed within curved portion of the vasculature. Depending on the target site, the curved portion may be the aortic arch, the transition from the inferior vena cava to the atrial septum, the iliac bifurcation (for access from on iliac artery to its contralateral iliac artery), the brachiocephalic trunk or the aorta of the patient artery or the aortic arch (for trans-radial access to the renal arteries), or other tortuosity that may be encountered between the entry point and the target site. For example, for access to the left atrium of a patient, from the femoral vein, the curve of the right atrium is expected be located about 55 to 65 cm from the entry point into the vasculature (a cut-down in the thigh of the patient). Thus the steerable catheter for access to the atrial septum from the femoral vein is constructed such that, when the inserted in the vasculature, with the deflectable segment disposed within the right atrium, proximate the atrial septum of the patient (where deflection facilitates crossing into the left atrium of the patient), the wound segment is disposed, in curved configuration, across the right atrium. This can be accomplished, as indicated in the table above, with a steerable catheter having a 5 cm deflectable segment at the distal and of the steerable catheter, followed by a 10 cm wound segment, followed by a proximal segment of at least 55 cm (the proximal segment lengths described in the table may be considered minimum lengths). This relationship between the steerable catheter structure and the vasculature of a patient is shown in FIG. 7, which illustrate the steerable catheter 1 used to access portions of the heart 30, with the steerable catheter disposed within the vasculature of a patient, in the pathway leading from the femoral vein, up the inferior vena cava 31, through the right atrium 32, through the atrial septum 33 an into the left atrium 34, such that the deflectable segment 2d is disposed proximate the target site of the left atrium and the wound segment 2w is disposed, in a curved configuration, along around the curve leading from the vena cava to the atrial septum. The proximal segment 2p extends downs the inferior vena cava to the entry point in the femoral vein. In use, the steerable catheter is inserted into the vasculature, navigated through the vasculature until the deflectable segment of the steerable catheter is disposed proximate the target site, and, with a properly sized steerable catheter, the wound segment is disposed across a curve in the vasculature. Once properly placed, the deflectable segment can be deflected by operation of one or more pull wires (tensioning or releasing tension), through manipulation of the steering mechanism on the proximal handle. During manipulations of the pull wires and deflection of the deflectable segment, the wound segment, by virtue of the wound nature of the pull wires, will experienced circumferentially balances forces and be much less likely to change its configuration or experience whipping common in other steerable catheters. The method can be used to access many target sites, including each of the target sites listed in the table, through corresponding insertion sites.

Though the steerable catheter has been described in relation to guide catheters, guide sheaths and introducer sheaths, the inventive aspects of the steering mechanisms can be adapted to any catheter. Thus, while the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of accessing a target site in left atrium of a patient, said method comprising the steps of:
   providing a steerable catheter comprising:
   a tube (2) having a proximal end (4), a distal end (5), and a lumen extending therebetween, said tube (2) having a first segment (2d) proximate said distal end and a second segment (2w) that extends proximally from said first segment (2d) toward said proximal end,
   a first pull wire (12) disposed within a first side lumen of the tube (2) and a second pull wire (13) disposed within a second side lumen of the tube (2), and extending from the distal end (5) to the proximal end (4) of the tube (2), said first and second pull wires comprising first and second wound segments (12w, 13w) which are wound about a longitudinal axis of the tube in the second segment (2w) of the tube, with the first wound segment (12w) and the second wound segment (13w) dispersed circumferentially about the longitudinal axis of the tube (2); wherein the wound segments (12w, 13w) are configured to reduce whipping when the tube (2) is rotated around the longitudinal axis of the tube (2), a handle (3) fixed to the tube (2), said handle comprising:
   means for selectively tensioning the first pull wire without tensioning the second pull wire, or tensioning the second pull wire without tensioning the first pull wire, to provide bidirectional steering of the deflectable segment;
   inserting the steerable catheter through the inferior vena cava and through right atrium and through the atrial septum of the patient until the first segment of the tube is disposed proximate the target site of the left atrium and the second segment is disposed, in a curved configuration, along the curve leading from the vena cava to the atrial septum; and
   operating one or both of the pull wires to deflect the first segment of the tube.

2. The method of claim 1, further comprising a step of:
   rotating the tube about the long axis of the tube (2) while the steerable catheter is disposed within the left atrium.

3. The method of claim 1, wherein:
   the steerable catheter is provided in a form in which the first pull wire (12) is wound in a first direction and the second pull wire (13) is wound in the first direction, substantially in parallel with the first pull wire.

4. The method of claim 1, wherein:
   the steerable catheter is provided in a form in which the first pull wire and second pull-wire are counter-wound.

5. The method of claim 1, wherein:
   the steerable catheter is provided in a form in which the first pull wire (12) extends proximally from the first wound segment (12w) in a straight proximal segment of the first pull wire (12p) and the second pull wire (13) extends proximally from the second wound segment (13w), in a straight proximal segment of the second pull wire (13p), and said straight proximal segment of the first pull wire (12p) and said straight proximal segment of the second pull wire (13p) extend proximally on opposite sides of the tube (2).

6. The method of claim 1, wherein the steerable catheter is provided in a form in which the steerable catheter comprises at least two pull wires, and the wound segments are dispersed about the circumference of the steerable catheter.

7. The method of claim 1, wherein the steerable catheter is provided in a form further characterized in that:
   the first pull wire (12) extends distally within the first segment (2d) of the tube (2) from the first wound segment (12w) in a straight distal segment of the first pull wire (12d) and the second pull wire (13) extends distally within the first segment (2d) of the tube (2) from the second wound segment (13w), in a straight distal segment of the second pull wire (13d), and said straight distal segment of the first pull wire (12d) and said straight distal segment of the second pull wire (13d) extend distally on opposite sides of the tube (2).

* * * * *